United States Patent
Hall et al.

(10) Patent No.: US 11,413,043 B2
(45) Date of Patent: Aug. 16, 2022

(54) ANCHOR DEVICE FOR VASCULAR ANASTOMOSIS

(71) Applicant: Merit Medical Systems, Inc., South Jordan, UT (US)

(72) Inventors: John Hall, North Salt Lake, UT (US); Wayne Mower, Bountiful, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 428 days.

(21) Appl. No.: 16/708,311

(22) Filed: Dec. 9, 2019

(65) Prior Publication Data

US 2020/0178969 A1 Jun. 11, 2020

Related U.S. Application Data

(62) Division of application No. 15/807,983, filed on Nov. 9, 2017, now Pat. No. 10,499,920.

(Continued)

(51) Int. Cl.
*A61B 17/11* (2006.01)
*A61F 2/06* (2013.01)
(Continued)

(52) U.S. Cl.
CPC ............. *A61B 17/11* (2013.01); *A61F 2/064* (2013.01); *A61F 2/07* (2013.01); *A61F 2/88* (2013.01);
(Continued)

(58) Field of Classification Search
CPC ........ A61F 2/064; A61F 2/2493; A61F 2/966; A61M 27/002; A61M 1/3655; A61B 17/11; A61B 2017/1135; A61B 2017/1107; A61B 17/0057; A61B 2017/00597; A61B 2017/1139
See application file for complete search history.

(56) References Cited

U.S. PATENT DOCUMENTS 3,357,432 A 12/1967 Sparks
3,435,823 A 4/1969 Edwards
(Continued)

FOREIGN PATENT DOCUMENTS

DE 4418910 12/1995
DE 29515546 3/1997
(Continued)

OTHER PUBLICATIONS

Office Action dated Oct. 6, 2021 for U.S. Appl. No. 15/934,152.
(Continued)

*Primary Examiner* — Katherine M Shi
(74) *Attorney, Agent, or Firm* — Dorsey & Whitney LLP

(57) ABSTRACT

The present disclosure relates to a medical anchor device and methods of use for providing an improved device for intraluminally directed vascular anastomosis. The anchor device includes a generally tubular graft having a flange disposed at one end thereof, where a portion of the graft extends through the flange. The flange includes a wire frame made of a resilient material and a thin membrane covering or overlaying the wire frame, where the wire frame is self-expanding when deployed within a lumen. The device may be deployed within the lumen at an anastomotic site without a need for sutures, staples, clips, or other mechanical attachment means that may cause further injury.

20 Claims, 7 Drawing Sheets

Related U.S. Application Data

(60) Provisional application No. 62/420,117, filed on Nov. 10, 2016.

(51) Int. Cl.
*A61F 2/07* (2013.01)
*A61F 2/88* (2006.01)
*A61F 2/966* (2013.01)
*A61B 17/00* (2006.01)

(52) U.S. Cl.
CPC ...... *A61F 2/966* (2013.01); *A61B 2017/0061* (2013.01); *A61B 2017/00597* (2013.01); *A61B 2017/00606* (2013.01); *A61B 2017/00853* (2013.01); *A61B 2017/1107* (2013.01); *A61B 2017/1135* (2013.01); *A61F 2210/0014* (2013.01); *A61F 2220/0008* (2013.01); *A61F 2230/0039* (2013.01)

(56) References Cited

U.S. PATENT DOCUMENTS

| | | |
|---|---|---|
| 3,490,438 A | 1/1970 | Lavender et al. |
| 3,683,926 A | 8/1972 | Suzuki |
| 3,814,137 A | 6/1974 | Martinez |
| 3,818,511 A | 6/1974 | Goldberg et al. |
| 3,826,257 A | 7/1974 | Buselmeier |
| 3,853,126 A | 12/1974 | Schulte |
| 3,882,862 A | 5/1975 | Berend |
| 3,998,222 A | 12/1976 | Shihata |
| 4,076,023 A | 2/1978 | Martinez |
| 4,133,312 A | 1/1979 | Burd |
| 4,184,489 A | 1/1980 | Burd |
| 4,214,586 A | 7/1980 | Mericle |
| 4,318,401 A | 3/1982 | Zimmernan |
| 4,427,219 A | 1/1984 | Madej |
| 4,441,215 A | 4/1984 | Kaster |
| 4,447,237 A | 5/1984 | Frisch et al. |
| 4,496,349 A | 1/1985 | Cosentino |
| 4,496,350 A | 1/1985 | Cosentino |
| 4,503,568 A | 3/1985 | Madras |
| 4,550,447 A | 11/1985 | Seiler, Jr |
| 4,619,641 A | 10/1986 | Schanzer |
| 4,655,771 A | 4/1987 | Wallersten |
| 4,723,948 A | 2/1988 | Clark et al. |
| 4,734,094 A | 3/1988 | Jacob et al. |
| 4,753,236 A | 6/1988 | Healy |
| 4,771,777 A | 9/1988 | Horzewski et al. |
| 4,772,268 A | 9/1988 | Bates |
| 4,786,345 A | 11/1988 | Wood |
| 4,790,826 A | 12/1988 | Elftman |
| 4,822,341 A | 4/1989 | Colone |
| 4,848,343 A | 7/1989 | Wallsten et al. |
| 4,850,999 A | 7/1989 | Planck |
| 4,877,661 A | 10/1989 | House et al. |
| 4,898,591 A | 2/1990 | Jang et al. |
| 4,898,669 A | 2/1990 | Tesio |
| 4,917,087 A | 4/1990 | Walsh et al. |
| 4,919,127 A | 4/1990 | Pell |
| 4,929,236 A | 5/1990 | Sampson |
| 4,955,899 A | 9/1990 | Della Corna et al. |
| 5,026,513 A | 6/1991 | House et al. |
| 5,041,098 A | 8/1991 | Loiterman et al. |
| 5,053,023 A | 10/1991 | Martin |
| 5,061,275 A | 10/1991 | Wallsten et al. |
| 5,061,276 A | 10/1991 | Tu et al. |
| 5,064,435 A | 11/1991 | Porter |
| 5,104,402 A | 4/1992 | Melbin |
| 5,171,227 A | 12/1992 | Twardowski et al. |
| 5,171,305 A | 12/1992 | Schickling et al. |
| 5,192,289 A | 3/1993 | Jessen |
| 5,192,310 A | 3/1993 | Herweck et al. |
| 5,197,976 A | 3/1993 | Herweck et al. |
| 5,282,860 A | 2/1994 | Matsuno et al. |
| 5,330,500 A | 7/1994 | Song |
| 5,336,616 A | 8/1994 | Livesey et al. |
| 5,399,168 A | 3/1995 | Wadsworth |
| 5,405,320 A | 4/1995 | Twardowski et al. |
| 5,405,339 A | 4/1995 | Kohnen et al. |
| 5,454,790 A | 10/1995 | Dubrul |
| 5,474,268 A | 12/1995 | Yu |
| 5,474,563 A | 12/1995 | Myler et al. |
| 5,476,451 A | 12/1995 | Ensminger et al. |
| 5,496,294 A | 3/1996 | Hergenrother et al. |
| 5,509,897 A | 4/1996 | Twardowski et al. |
| 5,558,641 A | 9/1996 | Glantz et al. |
| 5,562,617 A | 10/1996 | Finch, Jr. et al. |
| 5,562,618 A | 10/1996 | Cai et al. |
| 5,591,226 A | 1/1997 | Trerotola et al. |
| 5,607,463 A | 3/1997 | Schwartz et al. |
| 5,624,413 A | 4/1997 | Markel et al. |
| 5,637,088 A | 6/1997 | Wenner et al. |
| 5,637,102 A | 6/1997 | Tolkoff et al. |
| 5,645,532 A | 7/1997 | Horgan |
| 5,647,855 A | 7/1997 | Frooskin |
| 5,669,637 A | 9/1997 | Chitty et al. |
| 5,669,881 A | 9/1997 | Dunshee |
| 5,674,272 A | 10/1997 | Bush et al. |
| 5,676,346 A | 10/1997 | Leinsing |
| 5,743,894 A | 4/1998 | Swisher |
| 5,749,880 A | 5/1998 | Banas et al. |
| 5,755,773 A | 5/1998 | Schuster |
| 5,755,775 A | 5/1998 | Trerotola et al. |
| 5,755,778 A | 5/1998 | Kleshinski |
| 5,792,104 A | 8/1998 | Speckman et al. |
| 5,797,879 A | 8/1998 | Decampli |
| 5,800,512 A | 9/1998 | Lentz et al. |
| 5,800,514 A | 9/1998 | Nunez et al. |
| 5,800,522 A | 9/1998 | Campbell |
| 5,810,870 A | 9/1998 | Myers et al. |
| 5,830,224 A | 11/1998 | Cohn et al. |
| 5,840,240 A | 11/1998 | Stenoien et al. |
| 5,866,217 A | 2/1999 | Stenoien et al. |
| 5,904,967 A | 5/1999 | Ezaki et al. |
| 5,931,829 A | 8/1999 | Burbank et al. |
| 5,931,865 A | 8/1999 | Silverman et al. |
| 5,957,974 A | 9/1999 | Thompson et al. |
| 5,997,562 A | 12/1999 | Zadno-Azizi |
| 6,001,125 A | 12/1999 | Golds et al. |
| 6,019,788 A | 2/2000 | Butters et al. |
| 6,036,724 A | 3/2000 | Lentz et al. |
| 6,102,884 A | 8/2000 | Squitieri |
| 6,156,016 A | 12/2000 | Maginot |
| 6,167,765 B1 | 1/2001 | Weitzel |
| 6,171,295 B1 | 1/2001 | Garabedian |
| 6,231,085 B1 | 5/2001 | Olson |
| 6,245,098 B1 | 6/2001 | Feeser |
| 6,261,255 B1 | 7/2001 | Mullis et al. |
| 6,261,257 B1 | 7/2001 | Uflacker et al. |
| 6,280,466 B1 | 8/2001 | Kugler et al. |
| 6,308,992 B1 | 10/2001 | Mitsui et al. |
| 6,309,411 B1 | 10/2001 | Lashinski et al. |
| 6,319,279 B1 | 11/2001 | Shannon et al. |
| 6,338,724 B1 | 1/2002 | Dossa |
| 6,398,764 B1 | 6/2002 | Finch, Jr. et al. |
| 6,402,767 B1 | 6/2002 | Nash et al. |
| 6,428,571 B1 | 8/2002 | Lentz et al. |
| 6,436,132 B1 | 8/2002 | Patel et al. |
| 6,582,409 B1 | 6/2003 | Squitieri |
| 6,585,762 B1 | 7/2003 | Stanish |
| 6,610,004 B2 | 8/2003 | Mole et al. |
| 6,689,096 B1 | 2/2004 | Loubens et al. |
| 6,689,157 B2 | 2/2004 | Madrid et al. |
| 6,692,461 B2 | 2/2004 | Wantink |
| 6,699,233 B2 | 3/2004 | Slanda et al. |
| 6,702,748 B1 | 3/2004 | Nita et al. |
| 6,702,781 B1 | 3/2004 | Reifart et al. |
| 6,706,025 B2 | 3/2004 | Engelson et al. |
| 6,719,781 B1 | 4/2004 | Kim |
| 6,719,783 B2 | 4/2004 | Lentz et al. |
| 6,730,096 B2 | 5/2004 | Basta |
| 6,733,459 B1 | 5/2004 | Atsumi |
| 6,740,273 B2 | 5/2004 | Lee |
| 6,749,574 B2 | 6/2004 | O'Keefe |

(56) References Cited

U.S. PATENT DOCUMENTS

| | | |
|---|---|---|
| 6,752,826 B2 | 6/2004 | Holloway et al. |
| 6,758,836 B2 | 7/2004 | Zawacki |
| 6,858,019 B2 | 2/2005 | McGuckin, Jr. et al. |
| 6,926,735 B2 | 8/2005 | Henderson |
| 6,976,952 B1 | 12/2005 | Maini et al. |
| 6,981,987 B2 | 1/2006 | Huxel et al. |
| 7,011,645 B2 | 3/2006 | McGuckin, Jr. et al. |
| 7,025,741 B2 | 4/2006 | Cull |
| 7,036,599 B2 | 5/2006 | Matteucci |
| 7,101,356 B2 | 9/2006 | Miller |
| 7,131,959 B2 | 11/2006 | Blatter |
| 7,211,074 B2 | 5/2007 | Sansoucy |
| 7,244,271 B2 | 7/2007 | Lenz et al. |
| 7,244,272 B2 | 7/2007 | Dubson et al. |
| 7,252,649 B2 | 8/2007 | Sherry |
| 7,297,158 B2 | 11/2007 | Jensen |
| 7,399,296 B2 | 7/2008 | Poole et al. |
| 7,438,699 B2 | 10/2008 | Pecor et al. |
| 7,452,374 B2 | 11/2008 | Hain et al. |
| 7,507,229 B2 | 3/2009 | Hewitt et al. |
| 7,588,551 B2 | 9/2009 | Gertner |
| 7,708,722 B2 | 5/2010 | Glenn |
| 7,722,665 B2 | 5/2010 | Anwar et al. |
| RE41,448 E | 7/2010 | Squitieri |
| 7,762,977 B2 | 7/2010 | Porter et al. |
| 7,789,908 B2 | 9/2010 | Sowinski et al. |
| 7,828,833 B2 | 11/2010 | Haverkost et al. |
| 7,833,214 B2 | 11/2010 | Wilson et al. |
| 7,846,139 B2 | 12/2010 | Zinn et al. |
| 7,850,675 B2 | 12/2010 | Bell et al. |
| 7,850,705 B2 | 12/2010 | Bach et al. |
| 7,922,757 B2 | 4/2011 | McGuckin |
| 7,972,314 B2 | 7/2011 | Bizup et al. |
| 8,079,973 B2 | 12/2011 | Herrig et al. |
| 8,092,435 B2 | 1/2012 | Beling et al. |
| 8,313,524 B2 | 11/2012 | Edwin et al. |
| 8,512,312 B2 | 8/2013 | Sage |
| 8,690,815 B2 | 4/2014 | Porter et al. |
| 2001/0053930 A1 | 12/2001 | Kugler et al. |
| 2002/0049403 A1 | 4/2002 | Alanis |
| 2002/0055766 A1 | 5/2002 | Wallace et al. |
| 2002/0055771 A1 | 5/2002 | Sandock |
| 2002/0099432 A1 | 7/2002 | Yee |
| 2002/0151761 A1 | 10/2002 | Viole et al. |
| 2003/0100859 A1 | 5/2003 | Henderson et al. |
| 2003/0135258 A1 | 7/2003 | Andreas et al. |
| 2003/0135261 A1 | 7/2003 | Kugler et al. |
| 2003/0139806 A1 | 7/2003 | Haverkost et al. |
| 2003/0181969 A1 | 9/2003 | Kugler et al. |
| 2003/0212385 A1 | 11/2003 | Brenner et al. |
| 2003/0212431 A1 | 11/2003 | Brady et al. |
| 2003/0229365 A1 | 12/2003 | Whayne et al. |
| 2004/0024442 A1 | 2/2004 | Sowinkski et al. |
| 2004/0073282 A1 | 4/2004 | Stanish |
| 2004/0078071 A1 | 4/2004 | Escamilla et al. |
| 2004/0147866 A1 | 7/2004 | Blatter et al. |
| 2004/0193242 A1 | 9/2004 | Lentz et al. |
| 2004/0215337 A1 | 10/2004 | Hain et al. |
| 2004/0236412 A1 | 11/2004 | Brar |
| 2005/0004553 A1 | 1/2005 | Douk |
| 2005/0137614 A1 | 6/2005 | Porter et al. |
| 2005/0192559 A1 | 9/2005 | Michels et al. |
| 2005/0192604 A1 | 9/2005 | Carson et al. |
| 2005/0203457 A1 | 9/2005 | Smego |
| 2005/0209581 A1 | 9/2005 | Butts et al. |
| 2005/0215938 A1 | 9/2005 | Khan et al. |
| 2005/0273162 A1 | 12/2005 | Laguna |
| 2006/0004392 A1 | 1/2006 | Amarant |
| 2006/0058867 A1 | 3/2006 | Thistle et al. |
| 2006/0064159 A1 | 3/2006 | Porter et al. |
| 2006/0081260 A1 | 4/2006 | Eells et al. |
| 2006/0118236 A1 | 6/2006 | House et al. |
| 2007/0078412 A1 | 4/2007 | McGuckin, Jr. et al. |
| 2007/0078416 A1 | 4/2007 | Eliasen |
| 2007/0078438 A1 | 4/2007 | Okada |
| 2007/0088336 A1 | 4/2007 | Dalton |
| 2007/0123811 A1 | 5/2007 | Squitieri |
| 2007/0135775 A1 | 6/2007 | Edoga et al. |
| 2007/0142850 A1 | 6/2007 | Fowler |
| 2007/0161958 A1 | 7/2007 | Glenn |
| 2007/0167901 A1 | 7/2007 | Herrig et al. |
| 2007/0168019 A1 | 7/2007 | Amplatz et al. |
| 2007/0173868 A1 | 7/2007 | Bachinski et al. |
| 2007/0191779 A1 | 8/2007 | Shubayev et al. |
| 2007/0197856 A1 | 8/2007 | Gellman et al. |
| 2007/0213838 A1 | 9/2007 | Hengelmolen |
| 2007/0219510 A1 | 9/2007 | Zinn et al. |
| 2007/0233018 A1 | 10/2007 | Bizup et al. |
| 2007/0249986 A1 | 10/2007 | Smego |
| 2007/0249987 A1 | 10/2007 | Gertner |
| 2007/0265584 A1 | 11/2007 | Hickman et al. |
| 2007/0293823 A1 | 12/2007 | Sherry |
| 2007/0293829 A1 | 12/2007 | Conlon et al. |
| 2008/0009781 A1 | 1/2008 | Anwar et al. |
| 2008/0027534 A1 | 1/2008 | Edwin et al. |
| 2008/0109069 A1 | 5/2008 | Coleman et al. |
| 2008/0132924 A1 | 6/2008 | McGuckin |
| 2008/0167595 A1 | 7/2008 | Porter et al. |
| 2008/0195125 A1 | 8/2008 | Hoffman |
| 2008/0221469 A1 | 9/2008 | Shevchuk |
| 2008/0306580 A1 | 12/2008 | Jenson et al. |
| 2009/0076587 A1 | 3/2009 | Cully et al. |
| 2009/0099649 A1 | 4/2009 | Chobotov et al. |
| 2009/0137944 A1 | 5/2009 | Haarala et al. |
| 2009/0179422 A1 | 7/2009 | Werth |
| 2009/0227932 A1 | 9/2009 | Herrig |
| 2009/0234267 A1 | 9/2009 | Ross |
| 2009/0318895 A1 | 12/2009 | Lachner |
| 2010/0198079 A1 | 8/2010 | Ross |
| 2010/0268188 A1 | 10/2010 | Hanson |
| 2010/0268196 A1 | 10/2010 | Hastings et al. |
| 2010/0268316 A1 | 10/2010 | Brenneman et al. |
| 2011/0015723 A1 | 1/2011 | Batiste et al. |
| 2011/0034886 A1 | 2/2011 | Elbe et al. |
| 2011/0054312 A1 | 3/2011 | Bell et al. |
| 2011/0112482 A1 | 5/2011 | Redd |
| 2011/0208218 A1 | 8/2011 | Ball |
| 2011/0257609 A1 | 10/2011 | Bizup et al. |
| 2011/0264080 A1 | 10/2011 | Lim et al. |
| 2011/0295181 A1 | 12/2011 | Dann et al. |
| 2012/0059305 A1 | 3/2012 | Akingba |
| 2012/0065652 A1 | 3/2012 | Cully et al. |
| 2012/0078202 A1 | 3/2012 | Beling et al. |
| 2012/0143141 A1 | 6/2012 | Verkaik et al. |
| 2013/0060268 A1 | 3/2013 | Herrig |
| 2013/0282108 A1 | 10/2013 | Houston et al. |
| 2013/0338559 A1 | 12/2013 | Franano et al. |
| 2014/0018721 A1 | 1/2014 | Gage et al. |
| 2014/0276215 A1 | 9/2014 | Nelson |
| 2014/0288638 A1 | 9/2014 | Knight et al. |
| 2015/0051532 A1 | 2/2015 | Tomko et al. |
| 2015/0094744 A1 | 4/2015 | Aghayev et al. |
| 2016/0129177 A1 | 5/2016 | Herrig |
| 2018/0078745 A1 | 3/2018 | Gray et al. |

FOREIGN PATENT DOCUMENTS

| | | |
|---|---|---|
| DE | 102008055587 | 8/2009 |
| EP | 1797831 | 6/2007 |
| JP | 62112567 | 5/1987 |
| JP | 04507050 | 12/1992 |
| JP | 05212107 | 8/1993 |
| JP | 06105798 | 4/1994 |
| JP | 09084871 | 3/1997 |
| JP | 09264468 | 7/1997 |
| JP | 2003501223 | 1/2003 |
| JP | 2008511414 | 4/2008 |
| WO | 198403036 | 8/1984 |
| WO | 199008509 | 8/1990 |
| WO | 199519200 | 7/1995 |
| WO | 199624399 | 8/1996 |
| WO | 1998034676 | 8/1998 |
| WO | 2000027299 | 5/2000 |
| WO | 200076577 | 12/2000 |

(56) References Cited

FOREIGN PATENT DOCUMENTS

| | | |
|---|---|---|
| WO | 200105447 | 1/2001 |
| WO | 200105463 | 1/2001 |
| WO | 2001028456 | 4/2001 |
| WO | 2004032991 | 4/2004 |
| WO | 2004112880 | 12/2004 |
| WO | 2006026687 | 9/2006 |
| WO | 2009046994 | 4/2009 |
| WO | 2009059371 | 5/2009 |
| WO | 2010059102 | 5/2010 |
| WO | 2011060386 | 5/2011 |
| WO | 2011153302 | 12/2011 |
| WO | 2012018917 | 2/2012 |
| WO | 2012125927 | 9/2012 |
| WO | 2015127254 | 8/2015 |

OTHER PUBLICATIONS

European Search Report dated May 12, 2020 for EP17869533.4.
Office Action dated Apr. 17, 2020 for U.S. Appl. No. 15/934,152.
Office Action dated Mar. 3, 2021 for U.S. Appl. No. 15/934,152.
Office Action dated Aug. 18, 2020 for U.S. Appl. No. 15/934,152.
European Search Report dated Jun. 8, 2005 for EP05006233.0.
European Search Report dated Dec. 3, 2013 for EP05793066.1.
International Preliminary Report dated Mar. 12, 2014 for PCT/US2012/053967.
International Search Report and Written Opinion dated Jan. 28, 2015 for PCT/US2014/049547.
International Search Report and Written Opinion dated Feb. 19, 2018 for PCT/US2017/060848.
International Search Report and Written Opinion dated Mar. 15, 2013 for PCT/US2012/053967.
International Search Report and Written Opinion dated May 3, 2013 for PCT/US2012/053967.
International Search Report and Written Opinion dated May 6, 1998 for PCT/US1998/001939.
International Search Report and Written Opinion dated Jun. 3, 2009 for PCT/US2009/035923.
International Search Report and Written Opinion dated Jun. 20, 2007 for PCT/US2006/044564.
International Search Report and Written Opinion dated Jul. 17, 2018 for PCT/US2018/023956.
Notice of Allowance dated Mar. 15, 2010 for U.S. Appl. No. 11/216,536.
Notice of Allowance dated Sep. 24, 2019 for U.S. Appl. No. 15/807,983.
Notice of Allowance dated Oct. 4, 2013 for U.S. Appl. No. 12/831,092.
Office Action dated Jan. 9, 2018 for U.S. Appl. No. 14/450,468.
Office Action dated Feb. 6, 2013 for U.S. Appl. No. 12/831,092.
Office Action dated Feb. 21, 2017 for U.S. Appl. No. 14/192,567.
Office Action dated Mar. 15, 2018 for U.S. Appl. No. 14/332,091.
Office Action dated May 5, 2010 for U.S. Appl. No. 10/962,200.
Office Action dated Jun. 9, 2016 for U.S. Appl. No. 14/192,567.
Office Action dated Jun. 15, 2017 for U.S. Appl. No. 14/192,567.
Office Action dated Aug. 7, 2017 for U.S. Appl. No. 14/450,468.
Office Action dated Aug. 12, 2010 for U.S. Appl. No. 10/962,200.
Office Action dated Aug. 15, 2016 for U.S. Appl. No. 14/332,091.
Office Action dated Sep. 20, 2012 for U.S. Appl. No. 12/831,092.
Office Action dated Oct. 27, 2015 for U.S. Appl. No. 14/192,567.
Office Action dated Nov. 26, 2007 for U.S. Appl. No. 10/962,200.
Office Action dated Nov. 29, 2019 for U.S. Appl. No. 15/934,152.
Office Action dated Dec. 5, 2017 for U.S. Appl. No. 14/995,270.
Office Action dated Dec. 20, 2017 for U.S. Appl. No. 14/192,567.
Office Action dated Dec. 30, 2016 for U.S. Appl. No. 14/450,468.
Clinical Reveiw of MTI, Onxy Liquid Embolization System, available at http://www.fda.gov/ohrms/dockets/ac/03/briefing/3975b1-02-clinical-review.pdf. accessed Aug. 29, 2005.
Gore Hybrid Product Brochure—Optimal Outflow wtih Expanded Treatment Options, ,Jan. 2013.
Besarab et al., Measuring the Adequacy of Hemodialysis Access, Current Opinion in Nephrology and Hypertension, Rapid Science Publishers ISSN ,1996 ,1062-4821.
Coulson MD, et al., Modification of Venous End of Dialysis Grafts: An Attempt to Reduce Neointimal Hyperplasia, Dialysis & Transplantation, vol. 29 No. 1 ,Jan. 2000 ,10-18.
Coulson MD, PHD, et al., A Combination of the Elephant Trunk Anastomosis Technique and Vascular Clips for Dialysis Grafts, Surgical Rounds ,Nov. 1999 ,596-608.
Kanterman, et al., Dialysis Access Grafts: Anatomic Location of Venous Stenosis and Results of Angioplasty, Interventional Radiology, vol. 195 No. 1, 195 ,Apr. 1995 ,135-139.
Kumpe, et al., Angioplasty/Thrombolytic Treatment of Failing and Failed Hemodialysis Access Sites: Comparison with Surgical Treatment, Progress in Cardiovascular Diseases, vol. XXXIV No. 4 , Jan./Feb. 1992 ,263-278.
Lin, et al., Contemporary Vascular Access Surgery for Chronic Haemodialysis, They Royal College of Surgeons of Edinburgh, J.R. Coll, Surg, Edinb., 41 ,Jun. 1996 ,164-169.
Peterson, et al., Subclavian Venous Stenosis: A Complication of Subclavian Dialysis, The Journal of American Medical Association, vol. 252 No. 24 ,Dec. 28, 1994 ,3404-3406.
Raju M.D., et al., Techniques for Insertion and Management of Complications, PTFE Grafts for Hemodialysis Access, Ann. Surg., vol. 206 No. 5 ,Nov. 1987 ,666-673.
Sharafuddin et al., Percutaneous Balloon-Assisted Aspiration Thrombectomy of clotted ahemodialysis Access Grafts, Journal of Vascular and Interventional Radiology, vol. 7 No 2 ,Mar.-Apr. 1996,177-183.
Office Action dated Jun. 15, 2021 for U.S. Appl. No. 15/934,152.
European Search Report dated Oct. 28, 2020 for EP18771028.0.
Notice of Allowance dated Oct. 2, 2020 for U.S. Appl. No. 15/933,815.

ANCHOR DEVICE FOR VASCULAR ANASTOMOSIS

RELATED APPLICATIONS

This application claims priority to U.S. application Ser. No. 15/807,983, filed on Nov. 9, 2017 and titled, "Anchor Device for Vascular Anastomosis," which claims priority to Provisional Application No. 62/420,117, field on Nov. 10, 2016 and titled, "Anchor Device for Vascular Anastomosis," both of which are hereby incorporated by reference in their entireties.

TECHNICAL FIELD

The present disclosure relates generally to anchor devices for medical uses. More specifically, the present disclosure relates to an anchor device for intraluminally directed vascular anastomosis and related methods of use.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

DETAILED DESCRIPTION

Figure 1:
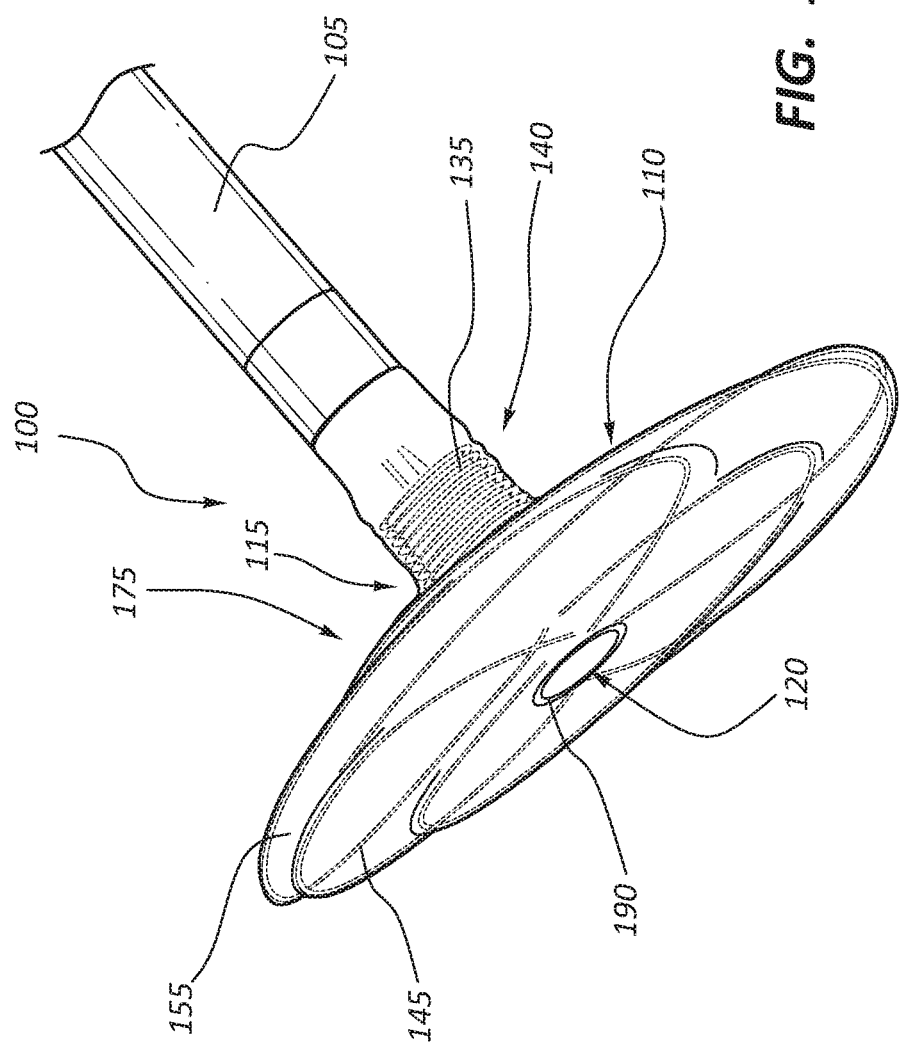
FIG. 1 is a perspective view of an embodiment of an anchor device.

The various embodiments disclosed herein generally relate to medical anchor devices and related methods of use. More specifically, the various embodiments relate to a medical anchor device configured for intraluminally directed vascular anastomosis, the anchor device designed to promote blood flow between adjoining blood vessels while minimizing or eliminating a need for sutures, staples, clips, adhesives, or other coupling techniques that may damage the surrounding anastomosed structures for securing the device within the body lumen. As is explained in further detail below, one advantage of the disclosed medical anchor device is the anchor device is designed to be self-supporting within the body lumen once deployed. In some embodiments, the medical anchor device comprises a self-expanding flange member attached to a reinforced stent graft and operable to adjoin the anastomosed structures for diverting blood flow as desired. Also disclosed herein are methods of utilizing a medical anchor device.

It will be appreciated that various features are sometimes grouped together in a single embodiment, figure, or description thereof for the purpose of streamlining the disclosure. Many of these features may be used alone and/or in combination with one another.

Embodiments may be understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including the devices disclosed herein. As used herein, the proximal portion of a medical device is the portion nearest a practitioner during use, while the distal portion is a portion at the opposite end. For example, the proximal end of a medical anchor device is defined as the end closest to the practitioner during insertion or utilization of the medical anchor device. The distal end is the end opposite the proximal end, along the longitudinal direction of the medical anchor device.

FIG. 1 illustrates an embodiment of a medical anchor device 100 that may be used for anastomotic procedures, such as vascular anastomosis for hemodialysis patients. It should be understood that while the detailed description may describe use of the medical anchor device 100 for vascular anastomosis, the anchor device 100 may be used for other anastomosis procedures in various biological systems in addition to the vascular system, such as the digestive system or the genitourinary system for example. Accordingly, the use of the medical anchor device 100 for vascular anastomosis is meant only as an example and is not meant to limit use of the anchor device 100 to the vascular system.

With reference to FIG. 1, the medical anchor device 100 includes a tubular graft 105 and a self-expanding flange 110 formed at a distal end 115 of the graft 105, with a portion of the graft 105 extended through the self-expanding flange 110 to provide an open passageway therethrough. In an example operation, once the medical anchor device 100 is deployed, the self-expanding flange 110 expands within the lumen 160 of a vessel (such as vessel 125 of FIG. 2) and applies a force to the lumen wall to serve as an anchor for the device 100 at an anastomotic site, with the graft 105 providing a passageway to redirect blood flow from a vessel (such as vessel 125 of FIG. 2) along a synthetic path or along another vessel. Additional details of the medical anchor device 100 and its operation are provide below with reference to the figures.

Figure 6:
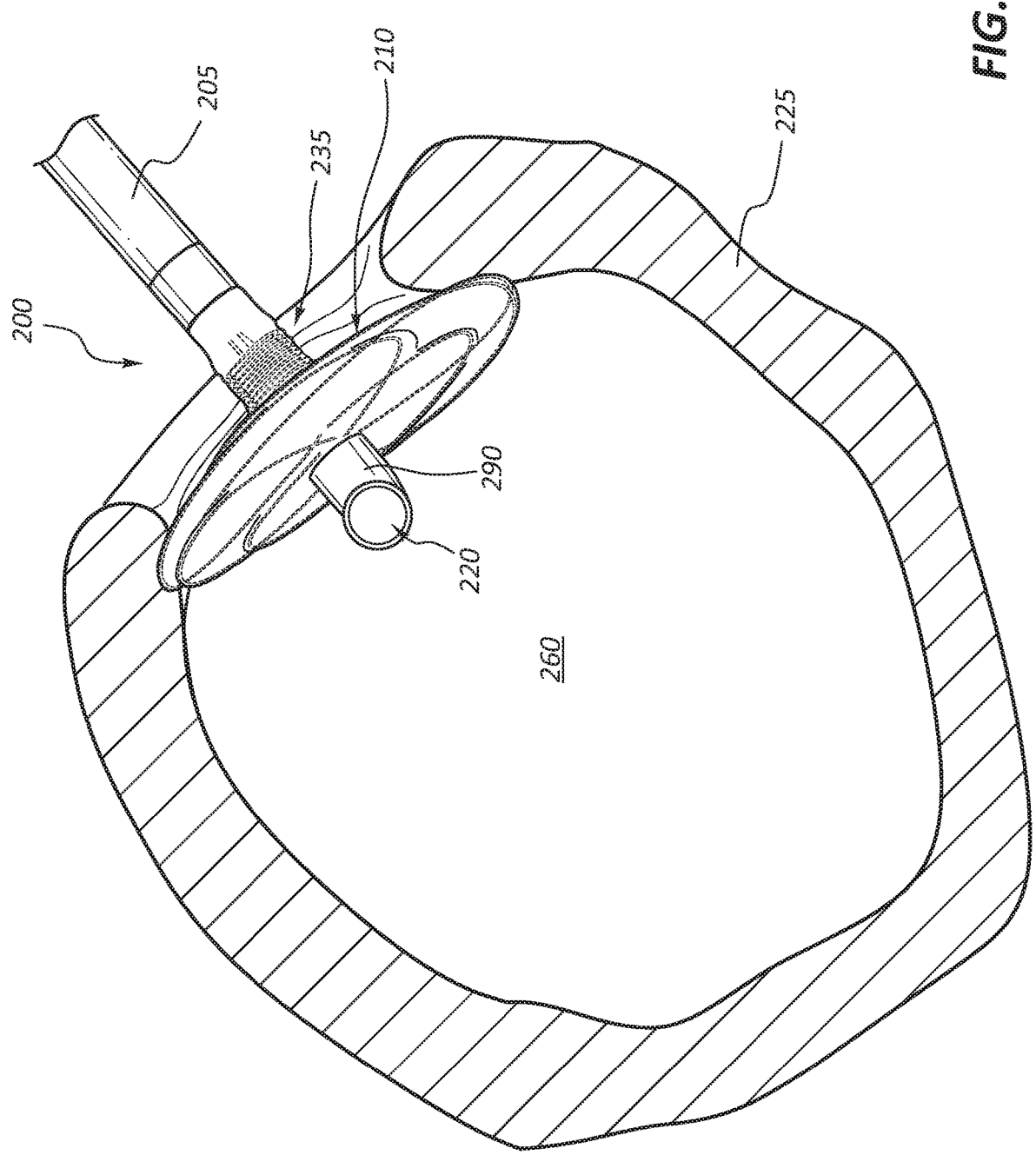
FIG. 6 is a side view of another embodiment of an anchor device with the anchor device disposed within a body lumen at an anastomotic site with the body lumen shown in cross-section.

With reference to FIG. 1, the tubular graft 105 is a generally elongate structure that may comprise one or more layers of any one of variety of bio-compatible materials, such as extruded tubes of polytetrafluoroethylene (PTFE) or other suitable materials. In some embodiments, one or more layers of the tubular graft 105 may have sufficient porosity to promote natural tissue ingrowth and cell endothelialization within or on the layer. In other embodiments, one or more layers of the tubular graft 105 may instead be configured to minimize tissue ingrowth, such as when the anchor device 100 is being used for short-term relief. The graft 105 includes a substantially central lumen 120 extending therethrough to permit the passage of blood therethrough once the graft 105 is deployed in the vascular system. In some embodiments, as illustrated in FIG. 1, the graft 105 may extend through the self-expanding flange 110 and have an end portion 190 flush against the self-expanding flange 110 to direct blood flow from a blood vessel (such as vessel 125 of FIG. 2). In other embodiments, the end portion 190 may not be flush against the self-expanding flange 110, but rather extend outwardly beyond the self-expanding flange 110 as illustrated in FIG. 6 to help promote blood flow. Additional details of this embodiment is further discussed in detail with particular reference to FIG. 6.

In some embodiments, some or all of the graft 105 may include a wire stent 135 to reinforce the graft 105. For example, as illustrated in FIG. 1, the graft 105 may include a first section 140 proximal to the flange 110 incorporating a wire stent 135 between two or more tubes of ePTFE. In such arrangement, the wire stent 135 provides additional stability and reinforcement of the graft 105, particularly adjacent the flange 110. The wire stent 135 may be formed in any one of a variety of suitable arrangements, such as an expanding stainless steel stent formed of stainless steel wire in a "zig-zag" pattern, a braided stainless steel stent, or a generally helical spring-like stent, for example.

With continued reference to FIG. 1, the self-expanding flange 110 includes a wire frame 145 generally splayed or fanned radially outwardly from a central axis of the flange 110. The wire frame 145 may be constructed from any one of a suitable shape memory alloy, such as a platinum-filled nickel-titanium alloy (Nitinol), which allows the flange 110 to expand once deployed within the blood vessel 125 as described in further detail below. Preferably, the shape memory alloy is selected such that it is sufficiently soft so as to minimize internal wall injury at the anastomotic site 150 as the flange 110 expands.

The flange 110 further includes a membrane 155 overlaying or covering the wire frame 145 to essentially form a disc-like shape for the flange 110. In some embodiments, the membrane 155 may be a thin layer of ePTFE material to promote tissue ingrowth at the anastomotic site 150 and aid in sealing the anastomosis from leakage. In other embodiments, the membrane 155 may be formed of other suitable biocompatible materials.

Figure 2:
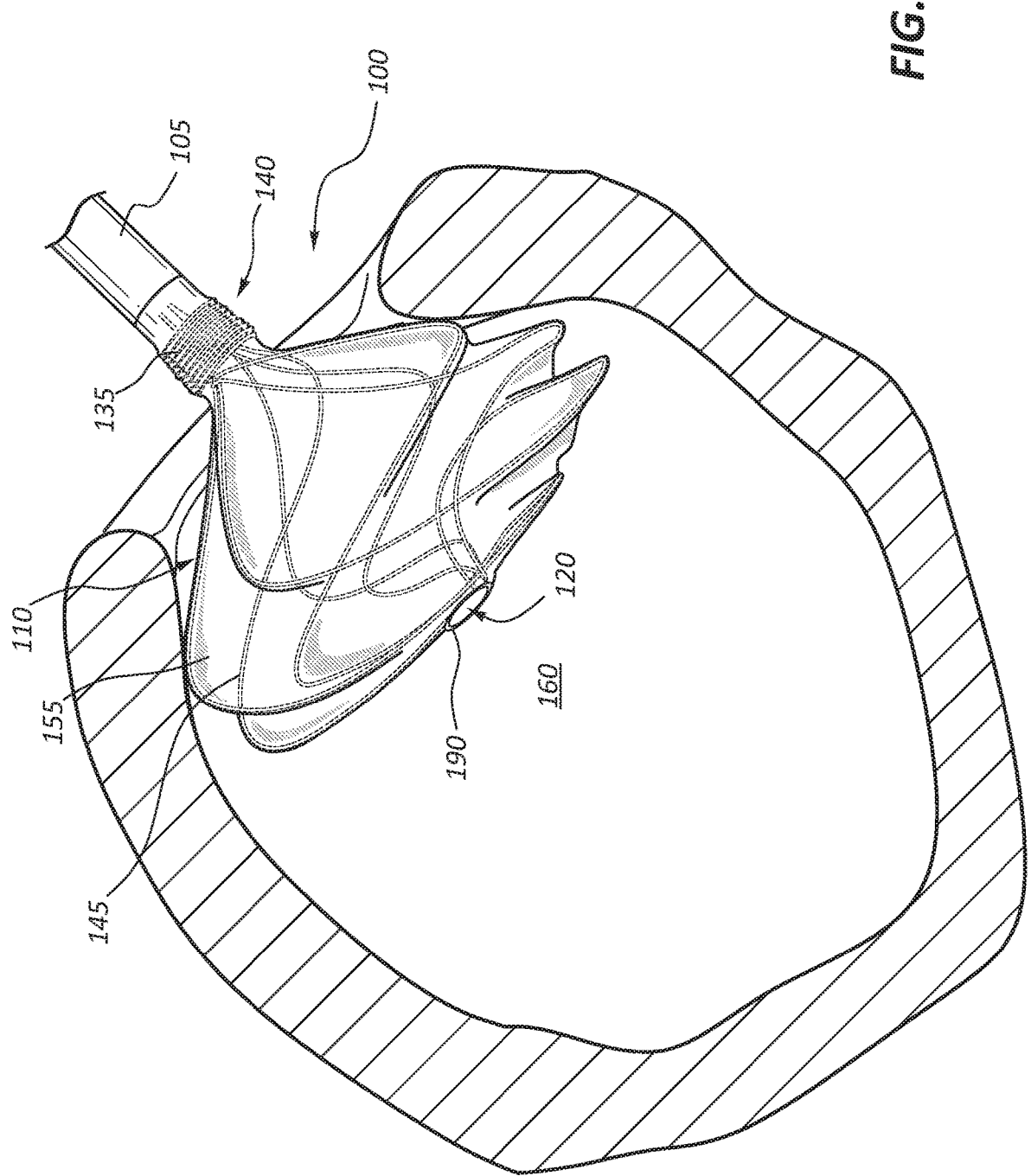
FIGS. 2 and 3 are side views of the anchor device of FIG. 1 illustrated in a partially deployed and fully deployed configuration, respectively, with the anchor device disposed within a body lumen at an anastomotic site with the body lumen shown in cross-section.
Figure 3:
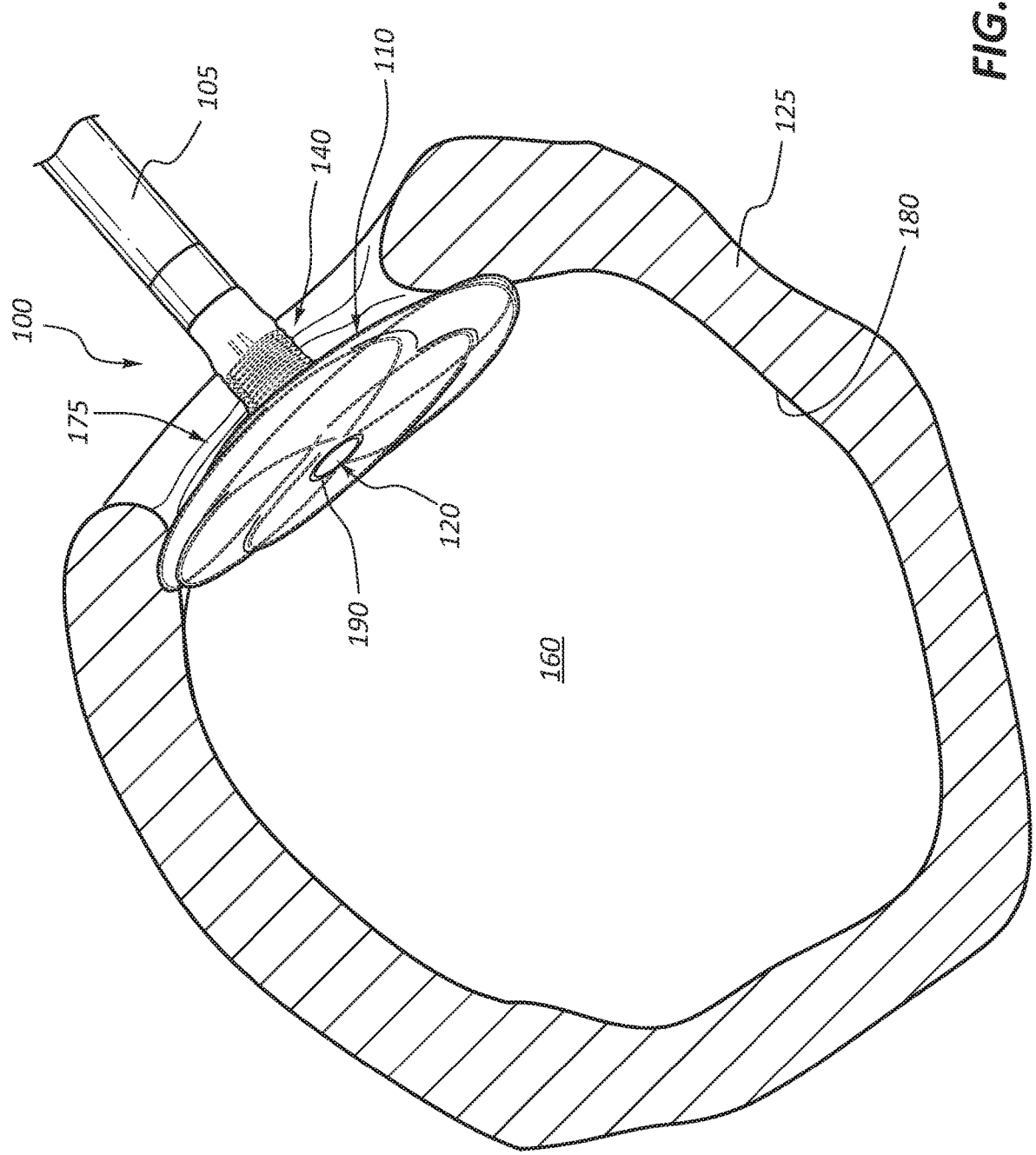
Figure 4:
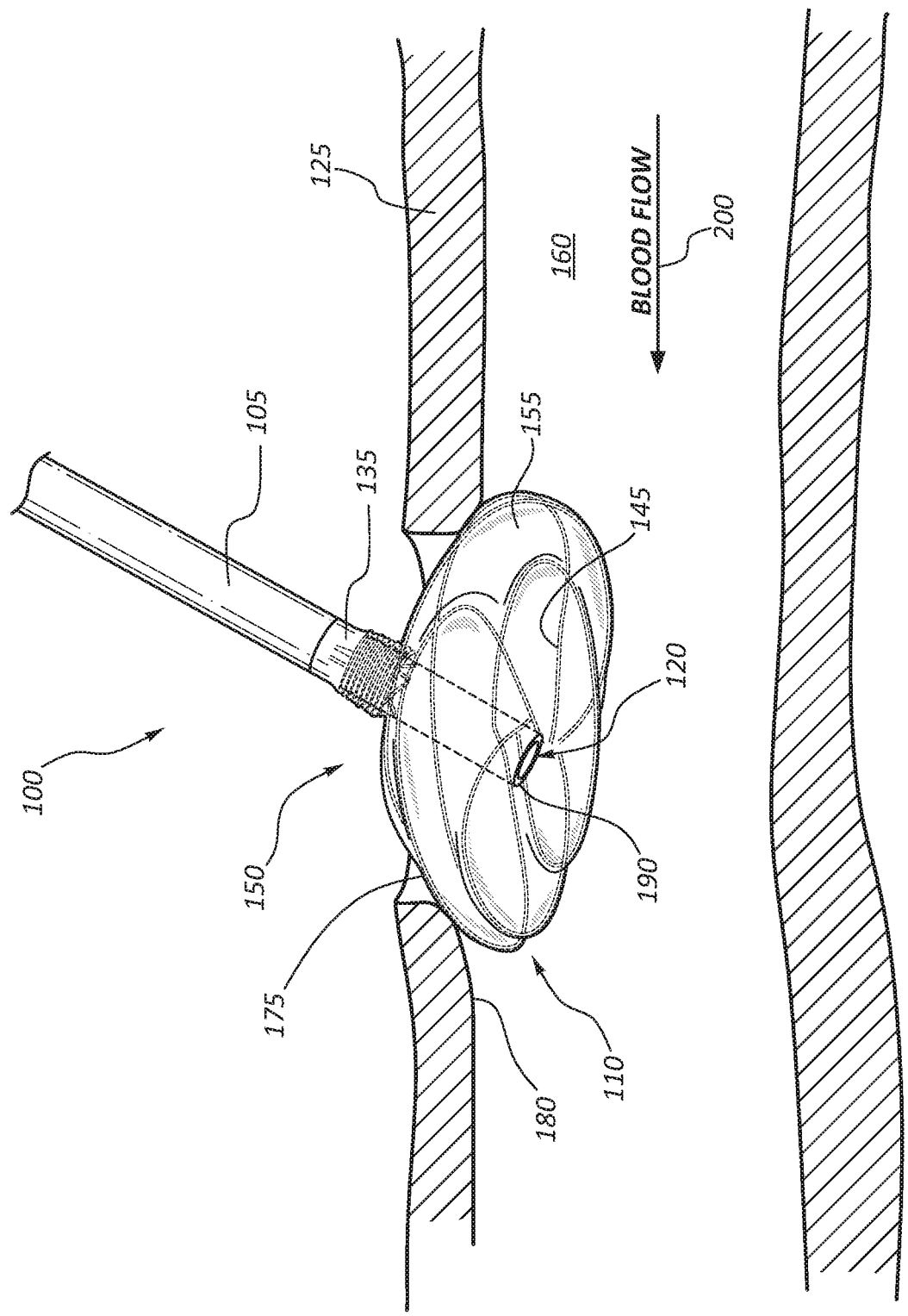
FIG. 4 is a side view of the anchor device and body lumen of FIG. 3, with the body lumen shown in cross-section through a plane disposed perpendicular to the cross-sectional plane of FIG. 3.

FIGS. 2-4 illustrate various views of the anchor device 100 of FIG. 1 disposed at an anastomotic site 150 within a body lumen 160 for creating an artificial pathway, for example, from an artery to a vein and forming the anastomosis along a continuous portion of the artery wall. With collective reference to FIGS. 2-4, the following sections describe additional details of an example deployment and use of the medical anchor device 100. In some embodiments, the anchor device 100 may be delivered to the anastomotic site 150 in accordance with conventional catheterization techniques. Accordingly, specific details relating to such techniques are not further described herein to avoid obscuring more pertinent details of the embodiments.

For context, the following provides a high-level summary of a conventional catheterization technique that may be used to deliver the anchor device 100 to the anastomotic site 150. It should be understood that the described technique is merely meant to illustrate one example delivery process, and others may be used in other embodiments without departing from the principles of the disclosed subject matter. In one example process, a needle is inserted into the patient's body and advanced toward a target blood vessel (e.g., an artery). Thereafter, a guidewire is inserted through the needle and advanced to the blood vessel. The guidewire is used to advance a delivery catheter toward the anastomotic site 150. With general reference to FIGS. 2-4, the following sections describe additional details relating to deployment of the anchor device 100.

With the delivery catheter in position, the anchor device 100 is advanced through the delivery catheter with the flange 110 being in a collapsed or contracted state. Once the anchor device 100 is ready for delivery within the intraluminal space 160 of the blood vessel 125, the delivery catheter is retracted, thereby exposing the flange 110. Removal of the delivery catheter causes the wire frame 145 of the flange 110 to expand radially from its contracted state to a normal resting state. For example, FIG. 2 illustrates the flange 110 in a partially deployed state, with the wire frame 145 partially expanded within the intraluminal space 160. FIGS. 3 and 4 illustrate the flange in a fully expanded configuration. In this configuration, a radially outward portion 175 of the flange 110 contacts the inner wall 180 of the blood vessel 125 to provide an anchoring point for the anchor device 100, and to create a seal with the inner wall 180, thereby preventing fluid leakage. Anchoring the flange 110 against the inner wall 180 of the vessel 125 also helps retain the anchor device 100 from migrating into the intraluminal space 160 of the blood vessel 125.

In some embodiments, after the device 100 is deployed, a tacking suture (not shown) may be used to secure the device 100 to the vessel wall 180 at the anastomosis. The tacking suture may pass through the vessel wall 180, through the device 100, and back through the vessel wall 180, and finally tied into place. In other embodiments, the anchor device may include a second flange that may be used to anchor the device and create a sealed condition at the anastomosis site. Additional details of this embodiment are discussed with particular reference to FIG. 7.

Because anastomosed structures may be composed of tissues that are susceptible to damage, the anchor device 100 may be configured so as to not be detrimental to the integrity of these tissues. In addition, the anchor device 100 may be positioned to ensure that the anastomosed blood vessels are free of leakage at the anastomosis site 150 and that the anchor device 100 does not significantly disrupt the flow of blood. Accordingly, in some embodiments, a guidewire or other device (not shown) may be used to firmly position the flange 110 against the inner wall 180 of the blood vessel 125 so that the anastomosed structures remain patent for allowing an uninterrupted flow of matter therethrough. For example, the flange 110 may include adjustment members operable to adjust the fit of the flange 110 at the anastomotic site 150 and accommodate the blood flow from the vessel 125 to another blood vessel.

As mentioned previously, in some embodiments, the flange 110 of the anchor device 100 may be configured to minimize tissue ingrowth to facilitate removal of the device 100. In some embodiments, the device 100 may be removable and/or exchangeable percutaneously. In other embodiments, the flange 110 may be retractable, into the graft 105 to allow the anchor device 100 to be removed from the anastomotic site.

As described previously with reference to FIGS. 1-4, the anchor device 100 may be used to create an artificial pathway from one blood vessel to another, such as from an artery to a vein. In other example embodiments, however, the anchor device 100 may instead be used to traverse a branch vessel and form a pathway therewith as illustrated in FIG. 5 and discussed in further detail below.

Figure 5:
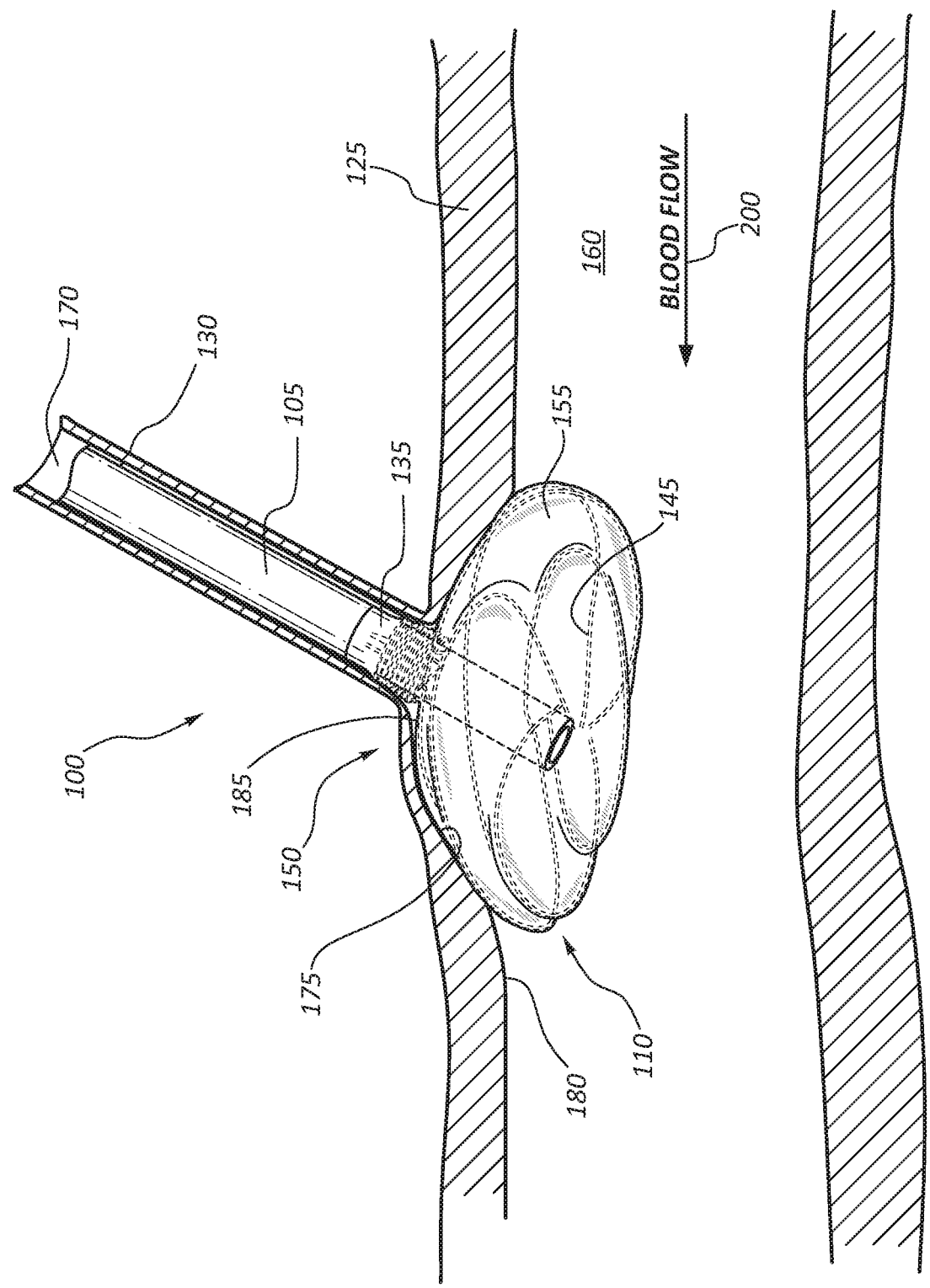
FIG. 5 is a side view of the anchor device of FIG. 1 illustrated in a deployed configuration between adjoining blood vessels in accordance with another embodiment.

With reference to FIG. 5, in one example deployment process, the delivery catheter (not shown) may be pushed through the intraluminal space 170 of a branch blood vessel 130 and partially into the intraluminal space 160 of the blood vessel 125. The delivery catheter is preferably advanced into the intraluminal space 160 to provide a pathway for positioning the flange 110 at least partially within the intraluminal space 160 of the blood vessel 125. With the delivery catheter in position, the anchor device 100 is advanced through the delivery catheter with the flange 110 being in a collapsed or contracted state. Once the anchor device 100 is ready for delivery within the intraluminal space 160, the delivery catheter is retracted, thereby exposing the flange 110. Removal of the delivery catheter causes the wire frame 145 of the flange 110 to expand radially from its contracted state to a normal resting state, with the flange 110 expanded in a similar fashion as illustrated in FIG. 1. In this configuration, a radially outward portion 175 of the flange 110 contacts the inner wall 180 of the blood vessel 125 to provide an anchoring point for the anchor device 100, with an inner portion 185 of the flange 110 overlaying the opening adjoining the vessels 125, 130.

FIG. 6 illustrates another embodiment of a medical anchor device 200 that may be used for anastomotic procedures, such as vascular anastomosis for hemodialysis patients. The medical anchor device 200 has many of the same or similar features, such as a graft 205, a self-expanding flange 210, and a wire stent frame 235, as the anchor device 100 described previously in FIGS. 1-5. Accordingly, such features will not be further described in detail herein to avoid repetition, with the understanding that the like features may have the same or substantial similar functionality as the respective features of the anchor device 100, unless described otherwise.

With particular reference to FIG. 6, in some embodiments, the medical anchor device 200 may include a distal end portion 290 of the graft 205 that extends outwardly beyond the self-expanding flange 210 to help promote blood flow. With reference to FIG. 6, once the flange 110 is firmly in positioned at the anastomotic site 150, a distal end 290 of the graft 205 is positioned within the intraluminal space 260 of the blood vessel 225, with an open end 295 of the graft 205 arranged relative to the direction of blood flow 200 such that blood flow is directed through the distal end 290 of the graft 205.

Figure 7:
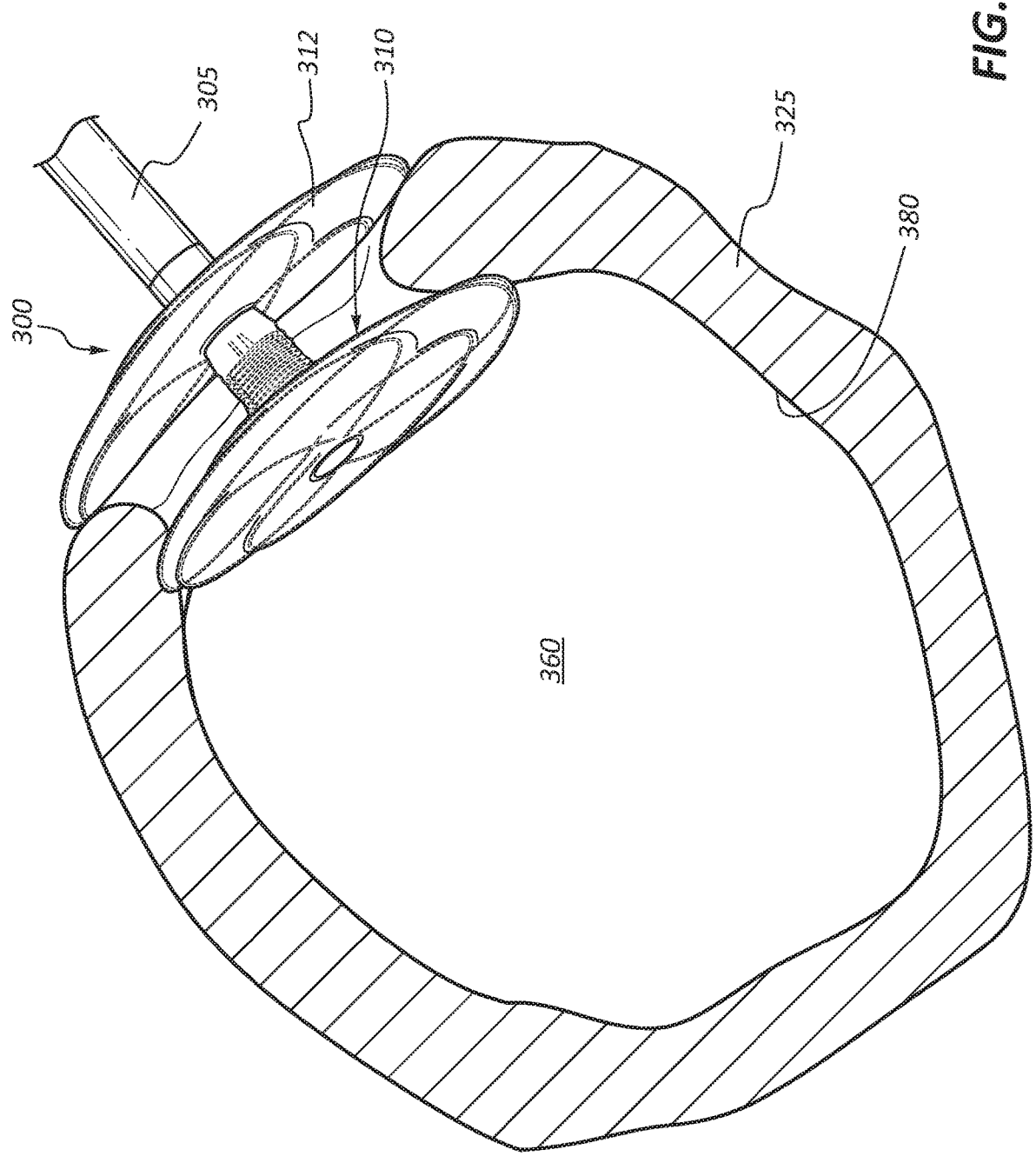
FIG. 7 is a side view of yet another embodiment of an anchor device with the anchor device disposed within a body lumen at an anastomotic site with the body lumen shown in cross-section.

FIG. 7 illustrates another embodiment of a medical anchor device 300 that may be used for anastomotic procedures, such as vascular anastomosis for hemodialysis patients. The medical anchor device 300 has many of the same or similar features, such as a graft 305, a self-expanding flange 310, and a wire stent frame 335, as the anchor device 100 described previously in FIGS. 1-5. Accordingly, such features will not be further described in detail herein to avoid repetition, with the understanding that the like features may have the same or substantial similar functionality as the respective features of the anchor device 100, unless described otherwise.

With particular reference to FIG. 7, the anchor device 300 includes a second a second flange 312 offset from the first flange 310, where the second flange 312 is deployed after the anchor device 300 is in position and the first flange 310 has been deployed. When the anchor device 300 is fully deployed, the second flange 312 is situated outside the blood vessel 325 and causes close apposition of both the first and second flanges 310, 312 to the blood vessel 325, thereby creating a sealed condition (e.g. prevents migration of the flange 310 toward the intraluminal space 360 and minimizes blood leakage across the anastomosis) at the anastomosis site 350.

Other configurations of the anchor device 100 are also contemplated. For example, in other embodiments, the flange 110 may be angled or sloped relative to the graft 105 to accommodate a variety of vasculature configurations that may not be amenable to an anchor device having a flange 110 that is perpendicular to the graft 105 (as illustrated in FIG. 1). In one embodiment, the flange 110 may be arranged at an angle of between 5 to 45 degrees relative to a central axis of the graft 105. In other embodiments, the flange 110 may be arranged at an angle of between 15 and 30 degrees. In still other embodiments, the flange 110 may be arranged at an angle between 45 and 90 degrees.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially straight" is recited with respect to a feature, it is understood that in further embodiments, the feature can have a precisely straight configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A method for positioning a medical anchor device at an anastomotic site in a body lumen of a patient, the method comprising:
   advancing a delivery sheath to the anastomotic site within the body lumen of the patient;
   disposing the medical anchor device within a lumen of the delivery sheath, the medical anchor device comprising:
      a generally tubular graft having a proximal portion and an opposite distal portion; and
      a first self-expanding flange disposed adjacent the distal portion of the tubular graft, the first self-expanding flange including an opening in communication with the graft to form a fluid passageway through the first self-expanding flange, the first self-expanding flange further including a wire frame having a plurality of resilient arms radiating outwardly from a central portion of the wire frame, and a membrane overlaying the wire frame; wherein upon displacement of the first self-expanding flange into the lumen of the delivery sheath the plurality of resilient arms collapse toward each other;
   advancing the medical anchor device through the delivery sheath toward the anastomotic site, wherein upon displacement of the first self-expanding flange out of the lumen of the delivery sheath and into the body lumen of the patient, the plurality of resilient arms are displaced away from each other; and
   positioning the first self-expanding flange within the body lumen of the patient to anchor the first self-expanding flange against one or more lumen walls, wherein a segment of the distal portion of the tubular graft is disposed within the body lumen of the patient.

2. The method of claim 1, wherein the first self-expanding flange is collapsible to a first state in response to application of a force, and expandable to a second state in response to an absence of the force.

3. The method of claim 1, further comprising adjusting a size of the first self-expanding flange via one or more adjustment members in communication with the first self-expanding flange to regulate fluid flow through the fluid passageway of the first self-expanding flange.

4. The method of claim 1, wherein the segment of the distal portion of the tubular graft extends through the first self-expanding flange and outwardly therefrom.

5. The method of claim 1, wherein positioning the first self-expanding flange within the body lumen of the patient, further includes disposing the proximal portion of the tubular graft within a branch body lumen branching from the body lumen of the patient.

6. The method of claim 1, wherein the positioning the first self-expanding flange within the body lumen of the patient, further comprises sealing the anastomotic site with the first self-expanding flange to prevent fluid leakage from the body lumen.

7. The method of claim 1, wherein the positioning the first self-expanding flange within the body lumen of the patient, further comprises adjusting a position of the first self-expanding flange to prevent disruption of fluid flow within the body lumen.

8. The method of claim 1, further comprising securing the medical anchor device to the one or more lumen walls, such that a tacking suture couples the one or more lumen walls to the medical anchor device.

9. The method of claim 1, wherein advancing the delivery sheath to the anastomotic site within the body lumen of the patient, comprises:
   inserting a needle into the body lumen of the patient;
   inserting a guidewire through the needle into the body lumen of the patient toward the anastomotic site; and
   advancing the delivery sheath over the guidewire to the anastomotic site.

10. The method of claim 1, further comprising positioning a second self-expanding flange outside of the body lumen of the patient.

11. The method of claim 1, further comprising retracting the delivery sheath from the anastomotic site to displace the first self-expanding flange out of the lumen of the delivery sheath.

12. A method of forming an artificial pathway between two body lumens of a patient, comprising:
   advancing a delivery sheath to a first anastomotic site within a first body lumen of the patient;
   disposing a medical anchor device within a lumen of the delivery sheath, the medical anchor device comprising:
      a generally tubular graft having a proximal portion and an opposite distal portion; and
      a first self-expanding flange disposed adjacent the distal portion of the tubular graft, the first self-expanding flange including an opening in fluid communication with the graft to form a fluid passageway through the first self-expanding flange, the first self-expanding-flange further including a wire frame having a plurality of resilient arms radiating outwardly from a central portion of the wire frame, and a membrane overlaying the wire frame; wherein upon displacement of the first self-expanding flange into the lumen of the delivery sheath the plurality of resilient arms collapse toward each other;
   advancing the medical anchor device through the delivery sheath toward the first anastomotic site, wherein upon displacement of the first self-expanding flange out of the lumen of the delivery sheath and into the first body lumen of the patient, the plurality of resilient arms are displaced away from each other; and
   positioning the first self-expanding flange within the first body lumen of the patient to anchor the first self-expanding flange against one or more lumen walls, wherein a segment of the distal portion of the tubular graft is disposed within the first body lumen.

13. The method of claim 12, further comprising:
   positioning the proximal portion of the tubular graft toward a second anastomotic site within a second body lumen of the patient; and
   coupling the proximal portion of the tubular graft to the second anastomotic site, wherein the second body lumen of the patient is in fluid communication with the first body lumen of the patient.

14. The method of claim 13, further comprising inducing fluid flow from the first body lumen of the patient, through the fluid passageway of the first self-expanding flange, through the tubular graft, through the second anastomotic site, and into the second body lumen of the patient.

15. The method of claim 12, further comprising securing the medical anchor device to the one or more lumen walls, wherein a tacking suture passes through the one or more lumen walls, through the medical anchor device, and back through the one or more lumen walls.

16. The method of claim 12, further comprising positioning a second self-expanding flange outside of the first body lumen of the patient.

17. The method of claim 12, wherein the positioning the first self-expanding flange within the first body lumen of the patient, further comprises sealing the first anastomotic site with the first expanding flange to prevent fluid leakage from the body lumen of the patient.

18. The method of claim 12, wherein the positioning the first self-expanding flange within the first body lumen of the patient, further comprises adjusting a position of the first self-expanding flange to prevent disruption of fluid flow within the first body lumen of the patient.

19. The method of claim 12, further comprising retracting the delivery sheath from the first anastomotic site to displace the first self-expanding flange out of the lumen of the delivery sheath.

20. A method for positioning a medical anchor device at an anastomotic site in a body lumen of a patient, the method comprising:
   obtaining an anastomotic kit, comprising:
      a needle;
      a guidewire;
      a delivery sheath; and
      a medical anchor device, comprising:
         a generally tubular graft having a proximal portion and an opposite distal portion; and
         a self-expanding flange disposed adjacent the distal portion of the tubular graft, the self-expanding flange including an opening in fluid communication with the graft to form a fluid passageway through the self-expanding flange, the self-expanding flange further including a wire frame having a plurality of resilient arms radiating outwardly from a central portion of the wire frame, and a membrane overlaying the wire frame;
   inserting the needle into the body lumen of the patient;
   inserting the guidewire through the needle into the body lumen of the patient toward an anastomotic site:
   advancing a delivery sheath over the guidewire to the anastomotic site;
   disposing the medical anchor device within a lumen of the delivery sheath, wherein the plurality of resilient arms of the self-expanding flange collapse toward each other;
   advancing the medical anchor device through the delivery sheath toward the anastomotic site, wherein upon displacement of the self-expanding flange out of the lumen of the delivery sheath and into the body lumen of the patient, the plurality of resilient arms are displaced away from each other; and
   positioning the self-expanding flange within the body lumen of the patient to anchor the self-expanding flange against one or more lumen walls, wherein a segment of the distal portion of the tubular graft is disposed within the body lumen of the patient.

* * * * *